(12) United States Patent
Niazi

(10) Patent No.: US 6,447,820 B1
(45) Date of Patent: Sep. 10, 2002

(54) PHARMACEUTICAL COMPOSITION FOR THE PREVENTION AND TREATMENT OF SCAR TISSUE

(76) Inventor: Sarfaraz K Niazi, 20 Riverside Dr., Deerfield, IL (US) 60015

( * ) Notice: Subject to any disclaimer, the term of this patent is extended or adjusted under 35 U.S.C. 154(b) by 0 days.

(21) Appl. No.: 09/681,137

(22) Filed: Jan. 22, 2001

(51) Int. Cl.[7] ........................ A61K 35/78; A61K 9/00; A61K 9/50; A01N 25/00
(52) U.S. Cl. ................. 424/767; 424/400; 424/502; 424/725; 514/946; 514/947
(58) Field of Search ................. 424/400, 502, 424/725, 767; 514/946, 947

(56) References Cited

U.S. PATENT DOCUMENTS 5,405,608 A * 4/1995 Xu .......................... 424/195.1
6,126,950 A * 10/2000 Bindra et al. ................ 424/401

OTHER PUBLICATIONS

Johnson, T. CRC Ethnobotany Desk Reference, 1999, CRC Press LLC, p. 568.*

* cited by examiner

Primary Examiner—Leon B. Lankford, Jr.
Assistant Examiner—Kailash C. Srivastava
(74) Attorney, Agent, or Firm—Welsh & Katz, Ltd.

(57) ABSTRACT

The disclosed is a treatment of existing and prevention of new skin scars in humans and animals using a topical application containing alcoholic extracts of *Cortex Phellodendri* and *Opuntia ficus indica* in a specific combination.

5 Claims, No Drawings

PHARMACEUTICAL COMPOSITION FOR THE PREVENTION AND TREATMENT OF SCAR TISSUE

BACKGROUND OF INVENTION

If an organ receives a physical trauma, such as an injury, surgery, a burn or an electric shock, or experiences inflammation as a result of a pathogenic cause, one of the inevitable consequences of the healing and inflammatory processes, which follow, is the formation of scar tissue. Scar tissue is formed as a result of the formation of a fibrin-platelet network following physical trauma or pathogenic inflammation, and the subsequent rebuilding and replacement of this network by granulation tissue.

The complex and typically highly irregular structure of the fibrin-platelet network, formed at an early stage after the trauma or as a result of inflammation, is of key importance in the fate of any wound healing process. Any physical structure, particularly filaments and membranes, whether diffusely or distinctly outlined, acts as a guide for the invading granulation tissue. This newly formed tissue is, in accordance with the mechanism described above, eventually rebuilt as scar tissue, organized is fibrous strands or membranes. The invading granulation tissue cells can practically never fully substitute for the original cells and, as a result, the tissue is never regenerated, but merely repaired. This is true for both the skin and for mucosal membranes, including those lining the body cavities, as well as other structures including muscles, tendons and nerves. Moreover, the scar tissue so formed may, in time, contract and remain contracted, deforming and disorganizing the injured area.

The proliferation and invasion of fibrin threads by even a few granulation tissue cells (including angiogenic cells) is usually sufficient to induce the formation of adhesions. The direction, density and organization of the individual fibrin threads in the fibrin-platelet network of the clot provides information, and determines the track to be taken by the invading granulation tissue cells, as well as by specific cells such as Schwann cells. Extracellular fibrin may deposit, stick to and establish abnormal bridges between adjacent structures. Thus, the structure of the fibrin-platelet network is of key importance in guiding the invading granulation tissue and thus in the formation of scar tissue.

Notwithstanding considerable literature on modalities of prevention of scar formation and removal of formed scar which have included the use of pressure dressings, splints, the application of silicone gel, steroid injections, protective devices, stretching devices, blood byproducts, protein solutions, gauzes, bandages, tapes and radiotherapy but all have had limited success and at times unwanted side effects.

Several patents have been granted for compositions claiming to prevent or treat human tissue scar formation, use of cactus and phellodendri. The following is a summary of some patents relevant to the invention described here.

European Patent Application EP 0 051 354 describes a polymeric substrate coated with the polysaccharide chitosan, to which is appended the antithrombotic agent heparin.

The U.S. Pat. No. 5,116,824 describes a composite material comprising an N-acylchitosan and collagen, which is suitable for, wound dressings. Heparin may be incorporated as an antithrombotic agent.

The U.S. Pat. No. 6,159,494 to Widgerow, et al., describes a method whereby postoperative scars are treated by a method of applying a microporous paper tape to the scar running along the length of the scar. A contact medium is applied to the exposed surface of the tape and penetrates to the skin. The contact medium comprises an expressed gel from the plant *Bulbine frutescens* and may contain asiaticoside and panthenol.

The U.S. Pat. No. 6,120,520 to Saadat, et al., is for an apparatus and methods for stimulating revascularization and tissue growth having a directable end region carrying a tissue piercing end effector. The apparatus optionally includes electrodes for depositing RF energy to form a controlled degree of scar tissue formation, means for delivering a controlled amount of a bioactive agent at the treatment site, or both.

The U.S. Pat. No. 6,127,348 to Roufa, et al., comprises the discovery that biocompatible anionic polymers can effectively inhibit fibrosis, scar formation, and surgical adhesions.

The U.S. Pat. No. 6,110,459 to Mickle, et al., is for a method is provided for forming a graft in heart tissue which comprises the transplantation of cells chosen from cardiomyocytes, fibroblasts, smooth muscle cells, endothelial cells and skeletal myoblasts.

The U.S. Pat. No. 6,093,388 to Fergusons is for treating fibrotic disorders using mannose-6-phosphate composition.

The U.S. Patent to Sawyer, et al., is for the inhibitors, obtainable from tissue or secretions of leeches typically of the order Rhynchobdellida to include the treatment of Crohn's disease, tumor implantation, atherosclerosis, thrombotic microangiopathy, fibrous growths of the skin, acne, scar formation, membranous glomerulonephrits, cataracts, or infection with microfilarial nematodes.

The U.S. Pat. No. 5,994,325 to Roufa, et al., relates to the discovery that biocompatible anionic polymers can effectively inhibit fibrosis, scar formation, and surgical adhesions. The invention is predicated on the discovery that anionic polymers effectively inhibit invasion of cells associated with detrimental healing processes, and in particular, that the effectiveness of an anionic polymer at inhibiting cell invasion correlates with the anionic charge density of the polymer.

The U.S. Pat. No. 5,981,606 to Martin pertains to invention of therapeutic TGF-beta-wound healing compositions for reducing the formation of scar tissue and increasing the proliferation and resuscitation rate of mammalian cells using pyruvate, an antioxidant and a mixture of saturated and unsaturated fatty acids and TGF-beta (GF) to form TGF-beta-wound healing compositions (ILA–D+GF). This invention also pertains to methods for preparing and using the TGF-beta-wound healing compositions.

The U.S. Pat. No. 5,919,476 to Fischer, et al., is for a bandage in the form of a reinforced silicone gel sheet for the treatment of scar tissue.

The U.S. Pat. No. 5,902,609 to Lee is for an invention that pertains to a composition for controlling wound scar production containing a calcium antagonist and a protein synthesis inhibitor.

The U.S. Patent to Fabo U.S. Pat. No. 5,891,076 is for a hypertrophic scar dressing that includes silicone-gel on that side of the dressing, which lies against the user's skin when worn.

The U.S. Pat. No. 5,885,982 to Dolynchuk, et al., is for a method of treating or preventing hypertrophic scar tissue in human skin comprising applying topically an effective amount of a non-toxic amine compound that is a transglutaminase inhibitor having a free amino group is disclosed. The amine compound that is a transglutaminase inhibitor is also selective for inhibiting Type III collagen peptide cross-linking.

The U.S. Pat. No. 5,885,581 to Massand is for a dermatological composition for use in improving the appearance of scars comprising 20–30 parts by weight of polyethylene glycol 200, 0.005–0.03 parts by weight of preservative, 0.05–0.2 parts by weight of sorbic acid, 0.5–2 parts by weight of allantoin, 1–3 parts by weight of xanthan gum, 5–15 parts by weight of fluid onion extract (Extract Allium Cepa), dermatologically acceptable aqueous carrier 55–65 parts by weight.

The U.S. Pat. No. 5,789,445 to Schweiger is for a topical application of benzoyl perioxide to regions of tissue scarring of a composition comprising several ingredients commonly used in cosmetic products for reduction and a softening of scar tissue.

The U.S. Pat. No. 5,736,508 to McMichael is for methods to eliminate or reduce the appearance of scar tissue by administration of streptolysin O.

The U.S. Pat. No. 5,731,298 to Reinmuller is for a pharmaceutical composition for non-topical wound, scar and keloid treatment is described which contains cross-linked glycosaminoglycans and conventional pharmaceutical auxiliary and/or carrier substances. The pharmaceutical composition is preferably administered intralesionally e.g. by injection in the form of a gel containing water. The cross-linked glycosaminoglycans are also suitable for use as cosmetics and skin care products.

The U.S. Pat. No. 5,686,425 to Lee is for a composition and method that are effective in revitalizing scar tissue by introducing a bioactive substance having angiogenic activity into the scar tissue. The bioactive substance can be introduced by itself, or it can be introduced into the scar tissue in a timed-release form. The present invention is effective in treating stress urinary incontinence or localized muscular dysfunction.

The U.S. Pat. No. 5,662,904 to Ferguson et al., is for a composition for use in the treatment of wounds to inhibit scar tissue formation during healing, comprising an effective amount of an activity-inhibiting growth factor neutralizing agent or agents specific against all TGF-beta, except for TGF-beta..sub.3, and PDGF, together with a pharmaceutically acceptable carrier.

The U.S. Pat. No. 5,569,678 to Lee pertains to a method for controlling wound scar production by administering a calcium antagonist, alone or in a combination with or followed by a steroid, to the wound site.

The U.S. Pat. No. 5,555,162 to Lee is for a method for improving the size and appearance of a scar associated with a fibromatosis, a keloid, or a hypertrophic wound healing disorder comprises stimulating collagenase activity in the scar. Preferably, stimulating collagenase activity is accomplished by covering said scar with a thermal insulating material that elevates the surface temperature of the scar.

The U.S. Pat. No. 5,532,275 to Grumet is for treating wounds that is based on the system and/or topically administration of an effective amount, of para-amino benzoic acid or its derivatives.

The U.S. Pat. No. 5,520,926 to Ferguson is where mannose-6-and 1-phosphates and their pharmaceutically acceptable salts and bioprecursors thereof are useful in the treatment of fibrotic disorders.

The U.S. Pat. No. 5,194,248 to Holick is for providing vitamin D analogs to an individual with topical compositions comprising tachysterol and luministerol analogs are disclosed. Optionally, the compositions may comprise one or more sunscreen agents. Also disclosed are methods for treating decubitus or diabetic foot ulcers; ulcerative keratitis; psoriasis; wounds; and inhibiting scar formation by administering the pharmaceutical compositions comprising tachysterol or lumisterol analogs.

The U.S. Pat. No. 5,128,375 to Tanaka, et al., is a keloid treating agent comprising as an active ingredient ethanolamine or a pharmaceutically acceptable salt thereof which is useful for the treatment of keloid such as ture keloid, cicatrical keloid, hypertrophic scar, etc.

The U.S. Pat. No. 4,865,031 to O'Keefe is for a mesh like fabric for implantation beneath or within the dermis to control formation of scar tissue.

The U.S. Pat. No. 4,839,159 to Winter, et al., provides a composition comprising L-carnitine in a suitable vehicle for topical application in improving or healing skin conditions including wrinkling, dry or peeling skin, and burns (particularly sunburn), and in healing and prevention of scar formation, particularly that caused by infection by a pathogen.

The U.S. Pat. No. 4,772,591 to Meisner is for a method comprising administration of ascorbic acid, a source of biologically available calcium, a precursor or stimulant of epinephrine or nor-epinephrine selected from tyrosine and phenylalanine, and an anti-inflammatory substance selected from anti-inflammatory sugars, amino sugars and biocompatible acid addition salts thereof, and anti-inflammatory amino acids to treat or reduce or tissue degenerative effects of the inflammation associated with the natural wound healing process and promotes connective tissue (scar tissue) growth in the wound.

The U.S. Pat. No. 4,694,021 to Schweiger is for topical application to regions of tissue scarring of a composition comprised of several ingredients commonly used in cosmetic products, such as urea, which leads to a reduction and a softening of scar tissue.

The U.S. Pat. No. 6,174,855 to Hansson provides the use of a thrombin inhibitor in the manufacture of a product for use in the control of wound healing processes within the body, in particular, the inhibition or prevention of fibrin-related adhesion and/or scar tissue formation, as well as products for use in the control of wound healing processes within the body comprising polysaccharides (e.g., chitosans) and low molecular weight peptide-based thrombin inhibitors.

The U.S. Pat. No. 5,736,584 to Kunkel is for an insect repelling composition comprising mineral oil cactus extract made from the leaves and stem of the Prickly Pear cactus.

The U.S. Pat. No. 5,747,462 to Feuntes relates to the area of pharmacology; its objective is to solve the technical problem of inflammation, pain, pruritus and local hyperthermia in human beings and animal species. The composition and the subcompositions thereof are obtained from plants of the family Cactaceae the main methodological steps being a set of processes; production, purification, physicochemical quantification, biotherapeutic evaluation, biopharmaceutical formulation and molecular identification. From the molecular identification a set of molecules is recognized, comprising carbohydrates and an aromatic amine.

The U.S. Pat. No. 6,039,954 to Yu, et al., is for herbal compositions containing for the treatment of gastrointestinal disorders, in particular Irritable Bowel Syndrome (IBS). The compositions are formulated preferably with powdered herbs including phellodendri.

The U.S. Pat. No. 5,916,555 to Lee, et al., is for a pharmaceutical composition containing a combination of natural drugs for treatment of diabetes. More specifically, the present invention relates to a composition containing 17 kinds of main natural drugs, i.e. Cordyceps, *Bezoar bovis, Carthami flos, Astragali radix,* Hirudo, *Polygoni cuspidati radix, Polygonati falcati rhizoma, Euonymi lignum suberalatum, Corni fructus, Moutan cortex, Lycii cortex radicis, Lycii fructus, Atractylodis rhizoma alba, Atractylodis rhizoma, Coptidis rhizoma, Puerariae radix* and *Rehmaniae radix crudae.* In addition to 17 kinds of main natural drugs, if desired, the composition of the present invention can contain one or more supplementary natural drugs selected from the group consisting of *Liriopsis tuber, Cistanchis herba, Adenophorae radix, Salviae radix, Ginseng radix rubra, Anemarrhenae rhizoma, Pachymae fungus, Phellodendri cortex, Mori radicis cortex, Schizandrae fructus, Galli stomachichum corium, Trichosanthis radix, Rhei rhizoma, Dioscoreae rhizoma, Alisma rhizoma, Polygoni multiflori radix, Galla rhois, Formica fusca L., Sanchi ginseng,* Margaritum and Gecko.

The U.S. Pat. No. 5,908,628 to Hou provides compositions comprising talc, silkworm excrement, and ingredients of plants of species of the genera Stephania, Coix, Pinellia, Prunus, Phellodendron, Sophora, Tetrapanax, Stemona, Glycyrrhiza, Tripterygium, Forsythia and Siegesbeckia, wherein such compositions have analgesic, antipyretic, and antiflammatory properties. The present invention also provides methods of using such compositions for treating various diseases, including osteoarthritis and rheumatoid arthritis.

The U.S. Pat. No. 5,405,608 to Xu relates to a pharmaceutical composition mainly used for treating thermal injuries of warm blooded mammals and human. It is composed of 3 to 15% by weight of beeswax and 85 to 97% by weight of sesame oil extract of Huangqin, Huanglian, Huangbai, earthworm and poppy capsule. In the sesame oil extract, each of Huangqin, Huanglian, Huangbai, earthworm and poppy capsule is in an amount of 2 to 10 weight percent based upon the total weight of sesame oil.

The U.S. Pat. No. 5,344,648 to Haga, et al., is for a central nervous system activator comprising a body or a dried product of a plant belonging to Rutaceae, or an extraction product selected from the group consisting of a lower alkane insoluble portion thereof, a lower fatty acid ester extract of the lower alkane insoluble portion, a lower fatty acid ester-halogenated lower alkane soluble portion of the lower fatty acid ester extract, a limonin fraction of the lower fatty acid ester-halogenated lower alkane soluble portion, and an obacunone fraction of the lower fatty acid ester-halogenated lower alkane soluble portion and a central nervous system activator comprising a limonoid.

BRIEF SUMMARY OF INVENTION

There is provided the use of a specific composition containing extract of two herbs, namely, *Cortex Phellodendri* (Huangbo or Amur Cork tree bark) and *Opuntia ficus indica* (Cactus), extracted by a specific method and combined in a specific proportion as a treatment of existing body scars or prevention of scar tissue formation in the control of wound healing processes. The composition described here can be used for any type of anticipated scarring such as in surgery or for the amelioration of pre-existing scars. The composition is used for a few weeks to a few months depending on the stage and maturity of the scar wound and leaves a cosmetically improved skin surface that is also more functional physiologically and mechanically. The preferred composition described here contains only natural ingredients that have been proven safe for consumption by humans and animals.

DETAILED DESCRIPTION OF THE INVENTION

We have now found, surprisingly, that a specific combination of cactus extract and the extract of cortex phellodendri in an oily base comprising canola oil and wax significantly inhibits or prevents the formation of scar tissue following physical trauma or pathogenic inflammation, and may thus be used in the removal or prevention of scarring in human and animal body. The composition described here reverses the process of scar formed, particularly on a recently scarred tissue. Phellodendri is a common drug used in traditional Chinese medicine while Opuntia is rarely used in the Chinese medicine. A combination of these two herbs in specific proportions provides an ideal rather unexpected combination that is effective in treating all types of human and animal scars. (Traditional Chinese Medicine, X Yan., et al., Ashgate Publishing, Hampshire, England, 1999). The wound-healing constituent preferably comprises the active ingredients from the plant *Cortex phellodendri* and *Opuntia ficus-indica* (of the Cactacea family) as the main constituents. The reported pharmacologic properties of Opuntia include: analgesia, antiinflmmatory, antioxidative, affecting activity of aromatase and reductase, free radical scavenger, antiviral, lowering LDL cholesterol levels, glucose-6-phosphatase and fructose-1,6-diphosphatase activity, antidiabetic, a rich source of biologically active alkaloids and other nutritional elements often considered essential for tissue growth. The emollient properties of *Opuntia ficus-indica* have been reported (T. Johnson, CRC Ethnobotany Desk Reference, 199, CRC Press LLC, page 568). However, the mechanism of action purported here is not an emollient effect as a large number of efficient emollients fail to achieve the activity claimed here.

Huangbo (*Phellodendron amurense Rupr*) used in the invention is selected from one or more groups of *Phellodendron chinese Schneid, Plellodendron chinese Scheid* var. *glabriusculum Schneid, Phellodendron chinese Schneid* var. *omeiense Huang, Phellodendron Schneid* var. *yunnanense Huang* and *Phellodendron chinese Schneid* var. *falcutum Huang.* The bark or cortex is used. (A Dictionary of Chinese Materia Medica, Shanghai Science and Technology Press, 1988, pages 2031 to 2035). Phellendori contains berberine and palmitine alkaloids, polysacchcharides, it is immunosuppressive, bactericidal, anti-inflammatory, bile secretion stimulant, affects gastric secretions and has anti-acne properties. The invention of Xu (U.S. Pat. No. 5,405,608) teaches the use of this herb in combination with other herbs and animal tissue in treating surface burns. More specifically, Xu teaches that the presence of Huangbo reduces the scarring of the healing tissue. Our invention is distinct from Xu's invention in three distinct manners. First, Xu prepares the extract by boiling the herb in sesame oil whereas we have used alcoholic extract. It is well-known that the nature of chemical extracted depend entirely on the method of extraction. The abstracts given below show that Huangbo contains a large number of oil and water soluble components. In the invention of Xu only water-soluble components are extracted; thus our extract is significantly different in its chemical composition and thus the activity. Secondly, Xu claims that Huangbo can reduce the scarring of the burn wound but there is no mention of removing existing scars, which is an entirely different process of treatment than the one disclosed by Xu. Thirdly, Xu uses a specific combination of herbs and animal tissue, a composition that is different from the one we have invented. Xu does not make use of *Opuntia ficus-indica,* which is the major component of our invention.

The following are some of the published references reporting the parmacological and therapeutic properties of the constituents of Huangbai and Opuntia.

El Kossori R L, Villaume C, El Boustani E, Sauvaire Y, Mejean L, *Plant Foods Hum Nutr* 1998; 52(3);263–70: The proximate composition of pulp, skin and seeds of prickly pear cactus (*Opuntia ficus-indica*) was investigated and is reported on a dry weight basis. The most abundant component of the pulp and skin was ethanol-soluble carbohydrates. Pulp contained glucose (35%) and fructose (29%) while the skin contained essentially glucose (21%). Protein content was 5.1% (pulp), 8.3% (skin) and 11.8% (seeds). Starch was found in each of the three parts of the fruit. Pulp fibers were rich in pectin (14.4%), skin and seeds were rich in cellulose (29.1 and 45.1%, respectively). Skin was remarkable for its content of calcium (2.09%) and potassium (3.4%). Prickly pear is a neglected nutritional source, which should be more widely used because of its potential nutrient contribution.

Park E H, Kahng J H, Paek E A,*Arch Pharm Res* February 1998; 21(1):30–4: The ethanol extracts of *Opuntia ficus-indica* fructus (EEOF) and *Opuntia ficus-indica* stem (EEOS) were prepared and used to evaluate the pharmacological effects of cactus. Both the extracts inhibited the writhing syndrome induced by acetic acid, indicating that they contains analgesic effect. The oral administrations of EEOF and EEOS suppressed carrageenan-induced rat paw edema and also showed potent inhibition in the leukocyte migration of CMC-pouch model in rats. Moreover, the extracts suppressed the release of beta-glucuronidase, a lysosomal enzyme in rat neutrophils. It was also noted that the extracts showed the protective effect on gastric mucosal layers. From the results it is suggested that the cactus extracts contain anti-inflammatory action having protective effect against gastric lesions.

Jonas A, Rosenblat G, Krapf D, Bitterman W, Neeman I: *Urol Res* 1998;26(4):265–70: The cactus flower is deemed to be helpful in benign prostatic hyperplasia (BPH) therapy, Cactus flower extracts indeed inhibited aromatase and 5-alpha reductase activity in cultured foreskin fibroblasts, and also in human placental and prostatic homogenates. The finding that cactus flower extracts interfere concurrently in vitro with aromatase and reductase activity as well as with free radical processes suggests that these substances may prove beneficial in BPH treatment.

Loro J F, del Rio I, Perez-Saniana L, *J Ethnopharmacol* Nov. 1, 1999;67(2):213–8: Opuntia dillenii (Ker-Gawl) Haw is a cactus that belongs to the family Opuntiae. Lyophilized aqueous extract of the fruits of the plant, used in Canarian traditional medicine for gastrointestinal and bronchial troubles, was evaluated for analgesic and anti-inflammatory properties in rats and mice. The *Opuntia dillenii* extract (100–400 mg/kg, i.p.) inhibited, in a dose-related manner, carrageenan-induced paw edema in rats. A dose-dependent action was obtained against chemical (writhing test) and thermic (hot plate test) stimuli, respectively, with doses of 50 and 100 mg/kg.

Ahmad A, Davies J, Randall S, Skinner G R, *Antiviral Res* May 1996;30(2–3):75–85: An extract of the cactus plant *Opuntia streptacantha* inhibited intracellular virus replication and inactivated extra cellular virus. Inhibition of virus replication also occurred following pre-infection treatment—a favorable finding in terms of in-vivo limitation of virus disease.

Gurrieri S, Miceli L, Lanza C M, Tomaselli F, Bonomo R P, Rizzarelli E,: *J Agric Food Chem* Nov 20, 2000;48(11):5424–5431: In this work, Sicilian cultivars of prickly pear (*Opuntia ficus indica*) were partially characterized from a chemical point of view. The sugar content (mainly glucose and fructose) is very high (11–12%), and also L-ascorbic acid is present in considerable amount 31–38 mg/100 g). Among the transition metals, a high content of manganese (II) (1.7–2.9 ppm) and good amounts or iron(III) (0.6–1.2 ppm) and zinc(II) (0.3–0.4 ppm) were found. In particular, such ions appear to be present mainly in the thick skin of the fruit or "trapped" inside the pulp. Pectin methylesterase (PME) seems to be present in very small amount and/or is not highly active.

Uchoa A F, Souza P A, Zarate R M, Gomes-Filho E, Campos F A, *Braz J Med Biol Res* June 1998; 31(6):757–61: We describe here the isolation and characterization of a major albumin from the seeds of *Opuntia ficus-indica* (Cactaceae). This protein has a molecular mass of 6.5 kDA and was isolated by a combination of gel filtration chromatography and reverse-phase HPLC. The amino acid composition of this protein was determined and it was shown to have similarities with the amino acid composition of several proteins from the 2S albumin storage protein family. The N-terminal amino acid sequence of this protein is Asp-Pro-Tyr-Trp-Glu-Gln-Arg.

Fernandez M L, Lin E C, Trejo A, McNamara D J,*J Nutr* June 1994;124(6):817–24: Prickly pear pectin intake decreases plasma LDL concentrations by increasing hepatic apolipoprotein B/E receptor expression in guinea pigs fed a hypercholesterolemic diet.

Satta M A, Sisini A, *Boll Soc Ital Biol Sper* Sep. 30, 1964; 40(18):1109–10: Glucose-6-phophatase and fructose-1,6-diphosphatase activity in *Opuntia ficus indica.*

Trejo-Gonzalez A, Gabriel-Ortiz G, Puebla-Perez A M, Huizar-Contreras M D, Munguia-Mazariegos M R, Mejia-Arreguin S, Calva E:*J Ethnopharmacol* December 1996;55 (1):27–33: The hypoglycemic activity of a purified extract from prickly pear cactus (*Opuntia fuliginosa*) was evaluated on STZ-induced diabetic rats. Blood glucose and glycated hemoglobin levels were reduced to normal values by a combined treatment of insulin and Opuntia extract.

Fodriguez-Felix A, Cantwell M, *Plant Foods Hum Nutr* 1988;38(1):83–93: The composition and quality of edible tender stems or cladodes of 3 Prickly Pear Cactus species (*Opuntia amyclaea, O. ficus-indica,* and *O. inermis*) were studied at different stages of development. This traditional Mexican vegetable is called "nopalitos" in Spanish and "cactus leaves" in English. Cladodes harvested when 20 cm in length have the following average composition per 100 g: 91.7 g of water, 1.1 g of protein, 0.2 g of lipid, 1.3 g of ash, 1.1 g of crude fiber, 4.6 g of complex carbohydrates and 0.82 g of simple sugars, 12.7 mg of ascorbic acid and 28.9 micrograms of carotenes.

Ma W W, Jiang X Y, Cooks R G, McLaughlin J L, Gibson A C, Zeylemaker F, Ostolaza C N, *J Nat Prod* July–August 1986;49(4):735–7: Cactus alkaloids, LXI. Identification of mescaline and related compounds in eight additional species using tlc and ms/ms.

Woodard R W, Craig J C, Bruhn J G, *Acta Chem Scand B* 1978;B32(8):619–20: The absolute configuration of the cactus alkaloid (−)-calipamine.

Pardanani J H, McLaughlin J L, Kondrat R W, Cooks R G,: *Lloydia* November–December 1977;40(6):585–90: Agurell has previously detected (tlc, glc-ms) tyramine, 3-methoxytyramine, and two unknown alkaloids in the Peruvian cactus.

Lee H S, Eom K E, Eom D O, *J Pharm Biomed Anal* October 1999;21(1):59–63: For the simultaneous determination of berberine and palmatine from Phellodendri Cortex.

Park J I, Shim J K, Do J W, Kim S Y, Seo E K, Kwon H J, Lee T K, Kim J K, Choi D Y, Kim C H, *Glycoconj J* March 1999;16(3):247–52: Heteropolysaccharides were isolated from the Korean medicinal plant, *Phellodendri cortex* (Hwangbck), by hot water and alkali extractions. The extracted polysaccharides were fractionated into eight fractions and they are mainly composed of D-N-acetylglucosamine, D-galactose, D-mannose, and D-glucose. Among the polysaccharide fractions, Fr.-2 showed a potent B-lymphocyte-stimulating activity in a system using polyclonal antibody forming cells in C57BL/6XC3H mice at dosages of 2–10 mg. On the basis of their solubility in aqueous ethanol, four fractions of Fr-2-1to Fr.-2-4 were further obtained from the Fr.-2, and Fr-2-3 was divided into Fr.-2-3-1,2,3, and 4 by DEAE cellulose chromatography. The main activity was found in Fr.-2-3-2, which contained 100% (w/w) of carbohydrates and further purified to Fr.-2-3-2-2 by gel filtration chromatography using TSK Gel HW50S. Fr.-2-3-2-2, having a molecular weight of about 230 kDa, showed the highest B-cell-stimulating activity and the half-maximal concentration for B-lymphocyte-stimulating activity was ca. 2.2 microg/ml.

Mori H, Fuchigami M, Inoue N, Nagai H, Koda A, Nishioka I, *Planta med* October 1994;60(5):445–9: *Phellodendri Cortex* (bark of *Phellodendron amurense Rupr. Rutaceae*) was a component having the most potent suppressive effect on the cellular immune response among the 8 medical plants composing Unsei-in. In the present study, we isolated OB-1 and OB-5 from *Phelldendri Cortex* as the bilogically active principles to suppress local GvH reactions in mice. The results suggest that OB-1 and OB-5 suppress the induction phase but not the effector phase of the cellular immune response.

Uchivama T, Kamikawa H, Ogita Z, Yakugaku Zasshi September 1989 109(9):672–6: In chinese medicine, *Phellodendri Cortex* (*Phellodendron amurense Ruprecht*) has been used to treat the patient who suffers from gastroenteritis, abdominal pain or diarrhea. Berberine has been identified as a major component in this plant, and it has biological activities, such as bactericidal activity, anti-cholera toxin effect, anti-inflammatory effect, stimulative effect of bile secretion or bilirubin discharge. In the previous study, we have shown the presence of anti-inflammatory activity in the berberine-free fraction of the extract from this plant. In the present study, we also found anti-ulcer activity in the fraction. The fraction significantly inhibited the formation of ethanol-induced ulcer, aspirin-induced ulcer (s.c., p.o.) pylorus-ligated ulcer (p.o., i.d.) in rats, as well as that of stress ulcer in restrained and water-immersed mice (p.o.). In addition, gastric acid secretion was significantly reduced in pylorus-ligated rats by subcutaneous or intraduodenal administration of the fraction, but not by oral administration. These findings suggest that the suppression of ulcer formation may be due to the additive effect of the cytoprotection effect and the reduction of gastric acid secretion by administration of the berberine-free fraction.

Takase H, Imanishi K, Miura O, Yumioka E, Watanabe H, *Jpn J Pharmacol* March 1989;49(3):301–8: This report describes the features of the anti-ulcer effect of Oren-gedoku-to (OGT, a traditional Chinese medicine) and its component herb drugs. *Coptidis rhizoma* and *Phellodendri cortex* given orally dose-dependently inhibited the appearance of ethanol-induced gastric hemorrhagic lesions in a dose range of 25–100 mg/kg, but the formation of the lesions was not prevented by *Scutellariae radix* or *Gardeniae fructus* at the same doses. *Coptidis rhizoma, Phellodendri cortex* and *Gardeniae fructus* inhibited the gastric potential difference (PD) reduction induced by ethanol, whereas *Scutellariae radix* did not prevent the decrease in the PD reduction caused by ethanol. *Phellodendri cortex, Scutellariae radix* and *Gardeniae fructus* had no significant influence on the basal PD, while *Coptidis rhizoma* increased the basal PD. The four-herb drugs prevented gastric acid secretion induced by 2-deoxy-D-glucose, but the three drugs except for *Phellodendri cortex* showed little effect on pentagastrin-stimulation. These results suggest that the gastric mucosal protection by OGT is ascribed to *Coptidis rhizoma* and *Phellodendri cortex,* and its antisecretory effect is due to the four drugs.

Wada K, Yagi M, Matsumura A, Sasaki K, Sakata M, Haga M, *Chem Pharm Bull* (*Tokyo*) August 1990;38(8):2332–4: Isolation of limonin and obacunone from phellodendri cortex shorten the sleeping time induced in mice by alpha-chloralose-urethane.

Mori H, Fuchigami M, Inoue N, Nagai H, Koda A, Nishioka I, Meguro K, *Planta Med* February 1995;61(1):45–9: Previously we have isolated the quaternary base alkaloids, magnoflorine and phellodendrine, from *Phellodendri Cortex* (cortex of *Phellodendron amurense Rupr., Rutaceae*) as the biologically active principles to suppress local graft-versus-host (GvH) reactions in mice. Phellodendrine suppressed local semisyngeneic GvH reactions and systemic allogeneic GvH reactions in X-ray irradiated recipient mice. Phellodendrine also suppressed the induction phase of sheep red blood cell (SRBC)-induced delayed type hypersensitivity in mice and tuberculin-induced delayed type hypersensitivity in guinea pigs, but did not suppress the effector phase of these reactions. Surprisingly, phellodendrine, unlike prednisolone and cyclophosphamide, did not affect antibody production in mice to SRBC.

Higaki S, Nakamura M, Morohashi M, Hasegawa Y, Yamagishi T, *J Dermatol* December 1996;23(12):871–5: *Coptidis Rhizoma* (CR) and *Phellodendri Cortex* (PC) inhibited the growth of *P. acnes* significantly among the eight Kampo crude drugs examined. It was speculated that Kampo crude drugs such as CR and PC, are better than minocycline or erythromycin from the point of view of a progressive increase in MIC to *P. acnes* CR and PC, which were each an ingredient of OGT, might contain some components with strong antibacterial activity to *P. acnes.*

The inflammatory modulation and immune suppression property of the herbal combination described in this invention is thought to stop the conversion of the mature fibrocytes to myofibroblasts, the cell type known to be associated with thickened keloid type scars. Hydration is believed to reduce water vapor loss and to restore homeostasis to the scar. The oily base used in the composition described her serves the purpose of keeping the skin hydrated as an occlusive film is formed on the scar. the constituents of the herbs further add chemical molecules that act as humectants as well. The oil used in this discovery is also a rich source of natural sterols, which are known to affect the granulation of healing tissue. The pharmaceutically acceptable ointment may have the following composition:

[Preferred Composition of the Invention]

| | |
|---|---|
| *Cortex phellondendri* alcoholic extract equivalent | 10.0% |
| *Optunia ficus indica* alcoholic extract equivalent | 5.0% |
| Vegetable oil | 83–87% |
| Wax | 10.0% |

Whereas the above composition is a preferred composition, those familiar in the art of formulation can modify it for the purpose of delivery to skin, the active ingredients of the composition. The concentration of oil and wax can be modified as necessary to obtain a desirable consistency. The composition is prepared by extracting the constituents of herbs in Ethanol USP by soaking the herbs in it for a period of at least 14 days. The alcoholic extracts are then mixed with oil and heated slowly under vacuum to remove alcohol to less than 1% level in the formulation. The oil mixture is then strained through muslin cloth and an appropriate quantity of wax added. The ointment mixture is then stirred gently and heated to allow complete melting and mixing of wax. The warm preparation is then filled into appropriate containers and allowed to congeal before sealing.

The composition described in this invention is applied sparingly (conveniently less than 2 mL over 12 cm$^2$) to cover the entire scar. The process is continued until scar can be as little as three months as is evidenced by a mature white scar (in white skinned persons) or a mature flat scar (in persons of pigmented skin). The most critical time period, however for scar management is the first two to six weeks, and commencing therapy with the composition described here substantially improves the nature of healed wound, both cosmetically and functionally. The treatment may conveniently commence after the removal of the sutures, which normally occurs after about one to three weeks after the surgery. Patients react favorably to the ease of applying the described composition at least once a day and preferably twice a day. There is no need to cover the surface of application.

The composition described here can be used in the reducing the scarring resulting from plastic surgery, donor skin replacement, injury scars, pregnancy stretch marks, etc.

The composition described here has been successfully used to treat all types of scars and it has been equally beneficial, though the time period of treatment is much longer, in chronic scars. The longer a scar has existed, the longer it takes to change the structure of skin and in some instances of very chronic scars the success may be limited.

What is claimed is:

1. A method of the removal of scar tissue in humans and animals comprising applying to a skin surface a composition having:

1.0 to 25% of *Cortex phellodendri*

1.0 to 25% of *Opuntia ficus-indica*

5.0 to 20.0% of a wax; and

83%–87% olive oil thereby removing the scar tissue from the skin surface.

2. The method of claim 1 wherein the scar is a surgical scar, physical injury scar, acne, post-pregnancy stretch mark, natural scar, vaccination mark, chemical scar, burn scar, skin donation scar, skin deformation or a keloid.

3. The method of claim 1 wherein the composition is applied to a human or animal body, wherein the dosage forms are dressings, patch, bandage or gauze.

4. The method of claim 1, wherein the composition comprises ethanolic extracts of whole plant, plant root or any part of plants of *Cortex phellodendri* and *Opuntia ficus-indica*.

5. A method for preventing the formation of scar tissue in humans and animals including the step of topically applying to a skin surface a homogenized composition consisting essentially of:

| | |
|---|---|
| *Cortex phellodendri* | 10.0% |
| *Opuntia ficus-indica* | 5.0% |
| Olive Oil | 83–87% |
| Beeswax | 10.0% | thereby preventing the formation of scar tissue in humans and animals.

\* \* \* \* \*